US007421140B2

(12) United States Patent
Rottem

(10) Patent No.: US 7,421,140 B2
(45) Date of Patent: Sep. 2, 2008

(54) METHOD AND SYSTEM FOR ENHANCING THE QUALITY OF DEVICE IMAGES

(76) Inventor: Shraga Rottem, 69-40 Fleet St., Forest Hills, NY (US) 11355

( * ) Notice: Subject to any disclaimer, the term of this patent is extended or adjusted under 35 U.S.C. 154(b) by 624 days.

(21) Appl. No.: 10/471,315

(22) PCT Filed: Nov. 21, 2001

(86) PCT No.: PCT/US01/43888

§ 371 (c)(1),
(2), (4) Date: Feb. 19, 2004

(87) PCT Pub. No.: WO02/071917

PCT Pub. Date: Sep. 19, 2002

(65) Prior Publication Data
US 2004/0122307 A1 Jun. 24, 2004

(51) Int. Cl.
G06K 9/00 (2006.01)
G06K 9/40 (2006.01)
G06F 3/048 (2006.01)
G06F 19/00 (2006.01)

(52) U.S. Cl. .................... 382/254; 382/128; 715/764; 700/110

(58) Field of Classification Search ............ 382/124, 382/128–132, 254–275; 715/764–767; 700/83–85, 700/108–111, 186–195; 606/130
See application file for complete search history.

(56) References Cited

U.S. PATENT DOCUMENTS

| 4,835,690 | A | * | 5/1989 | Gangarosa et al. | 600/410 |
|---|---|---|---|---|---|
| 5,365,310 | A | * | 11/1994 | Jenkins et al. | 399/8 |
| 5,463,768 | A | * | 10/1995 | Cuddihy et al. | 714/37 |
| 5,566,092 | A | * | 10/1996 | Wang et al. | 700/159 |
| 5,687,250 | A | * | 11/1997 | Curley et al. | 382/112 |
| 6,014,471 | A | * | 1/2000 | Barkan et al. | 382/275 |
| 6,032,678 | A | * | 3/2000 | Rottem | 600/437 |
| 6,061,057 | A | * | 5/2000 | Knowlton et al. | 715/744 |
| 6,175,655 | B1 | * | 1/2001 | George et al. | 382/256 |
| 6,195,409 | B1 | * | 2/2001 | Chang et al. | 378/20 |
| 6,238,049 | B1 | * | 5/2001 | Griffin et al. | 351/243 |
| 6,275,559 | B1 | * | 8/2001 | Ramani et al. | 378/4 |
| 6,433,325 | B1 | * | 8/2002 | Trigg | 382/255 |
| 6,442,542 | B1 | * | 8/2002 | Ramani et al. | 707/3 |

(Continued)

OTHER PUBLICATIONS

K.E. Augustine, M.C. Stacy, and R.A. Robb, "Managing images with image BOSS," Proceedings of SPIE—vol. 3031, Medical Imaging 1997: Image Display, ☐Yongmin Kim, Editor, May 1997, pp. 458-468.*

Primary Examiner—Bhavesh Mehta
Assistant Examiner—Manav Seth
(74) Attorney, Agent, or Firm—Hunton & Williams LLP; Eugene C. Rzucidlo

(57) ABSTRACT

A system for improving the quality of medical images depicts a list of sub-optimal image situations. For each sub-optimal image situation, a list of at least one possible reason for the sub-optimal image situation is provided, sorted by the probability. For each reason in the list, a list of at least one remedy for said reason is provided. By navigating these lists, an inexperienced user of an item of imaging equipment is guided to obtain an optimal quality image.

6 Claims, 8 Drawing Sheets

U.S. PATENT DOCUMENTS 6,665,425 B1 * 12/2003 Sampath et al. ............. 382/112
6,778,684 B1 *  8/2004 Bollman ...................... 382/112
6,934,590 B2 *  8/2005 Ogawa ........................ 700/19
6,952,097 B2 * 10/2005 Schreck et al. .............. 324/309
7,304,754 B1 * 12/2007 Nakamura et al. ......... 358/1.15

* cited by examiner

METHOD AND SYSTEM FOR ENHANCING THE QUALITY OF DEVICE IMAGES

FIELD OF THE INVENTION

This invention is directed to device adjuncts used for the analysis of images of human body organs for medical diagnosis, or in non-medical industrial apparatus, in particular to improving the quality of these images.

BACKGROUND OF THE INVENTION

One of the basic diagnostic methods of determining the health conditions of a patient is the imaging of affected areas of the patient's body, regardless of whether the patient is complaining of a symptom or whether a medical anamoly was found based on testing for an unrelated condition. The type of imaging most properly utilized for an initial objective determination is usually dictated by the nature of the organ or part of the body exhibiting a specific condition (or which is being tested for determining if a condition exists), or the actual condition which is suspected.

Imaging devices (the term "imaging" as used herein includes optical, aural and any other sensory recordable state of an object or patient) include those devices that permit visual inspection of a site or cavity directly or by use of a lens system for optical enhancement, and devices which permit visual inspection of a site through analog or digital displays or the analysis of images resulting from the use of ultrasound waves (sonograms), magnetic resonance (MRI), computerized tomography (CT scans), nuclear medicine, x-rays or other imaging technology. Existing specific tools or devices used for imaging include laparoscopes, MRI and ultrasonogram devices, as well as hysteroscopes, arthroscopes, esophagoscopes, bronchoscopes, rectoscopes, laryngoscopes, otoscopes, ophthalmoscopes, colposcopes, microscopes, computed radiography, x-ray imaging, computed tomography, mammography, angiography, gamma camera and nuclear medicine instruments, boreoscopes (used for internal analysis of machinery) and the like, which are all well known diagnostic tools in the art.

Currently, imaging systems come in many configurations, with different probes and many types of accessories. For some imaging systems, such as ultrasound, the quality of the image depends on the person performing the scanning, since in that case the scanning is not performed by the system itself, as in the case of a CT scan or MRI. The potential user, however, usually has no indication as to the quality of images to be attained when scanning with any particular configuration, and many professionals know very little about the diagnostic equipment that they utilize. This situation is exacerbated by vendors who agressively market diagnostic equipment without providing the basics as to what standard can be achieved by a particular diagnostic system in terms of the image of a normal organ. Vendors of new, inexpensive, portable scanning systems witness increased sales to medical practitioners who have very limited experience in scanning. These professionals need to learn how to achieve the best possible images (referred to in the art as "gold standard" images) obtainable from their equipment.

For example, a user may have a good representative sonogram in mind of an ovary based on an image in a book where the authors used X and Y equipment, or from a conference where a lecturer showed images made with Z and W equipment, or from a hands-on course using Q and V equipment. A user, however, may have or be considering buying W equipment and may not have any reference for the best achievable image of an organ with that equipment, before even looking for pathologies. Even in clinics where gold standard imaging is the norm, the situation changes abruptly after regular hours, during nights and weekends when the most experienced staff members are no longer seeing patients.

Thus, there is a need for a system that can automatically help professionals who are inexperienced with a particular imaging device learn how to achieve gold standard levels of imaging in the absence of experienced professionals.

SUMMARY OF THE INVENTION

The system of the present invention is a new feature of the system described in U.S. Pat. No. 6,032,678, "Adjunct To Diagnostic Imaging Systems For Analysis Of Images Of An Object Or A Body Part Or Organ", to Rottem, the contents of which are incorporated herein by reference.

The system of the present invention permits gold standard images for each model of imaging device and for each images to be stored and accessible to the diagnostic software. Once an image has been displayed next to a gold standard image, the system of the present invention can present to the practitioner a selection of possibilities that characterize an image. Clicking on one of these possibilities presents the user with a listbox displaying a selection of problems, and by clicking on a problem the user is presented with a listbox of possible solutions. By navigating this display of choices, the user can learn how to obtain better quality images from specific equipment and configurations.

DETAILED DESCRIPTION OF THE INVENTION

Figure 1:
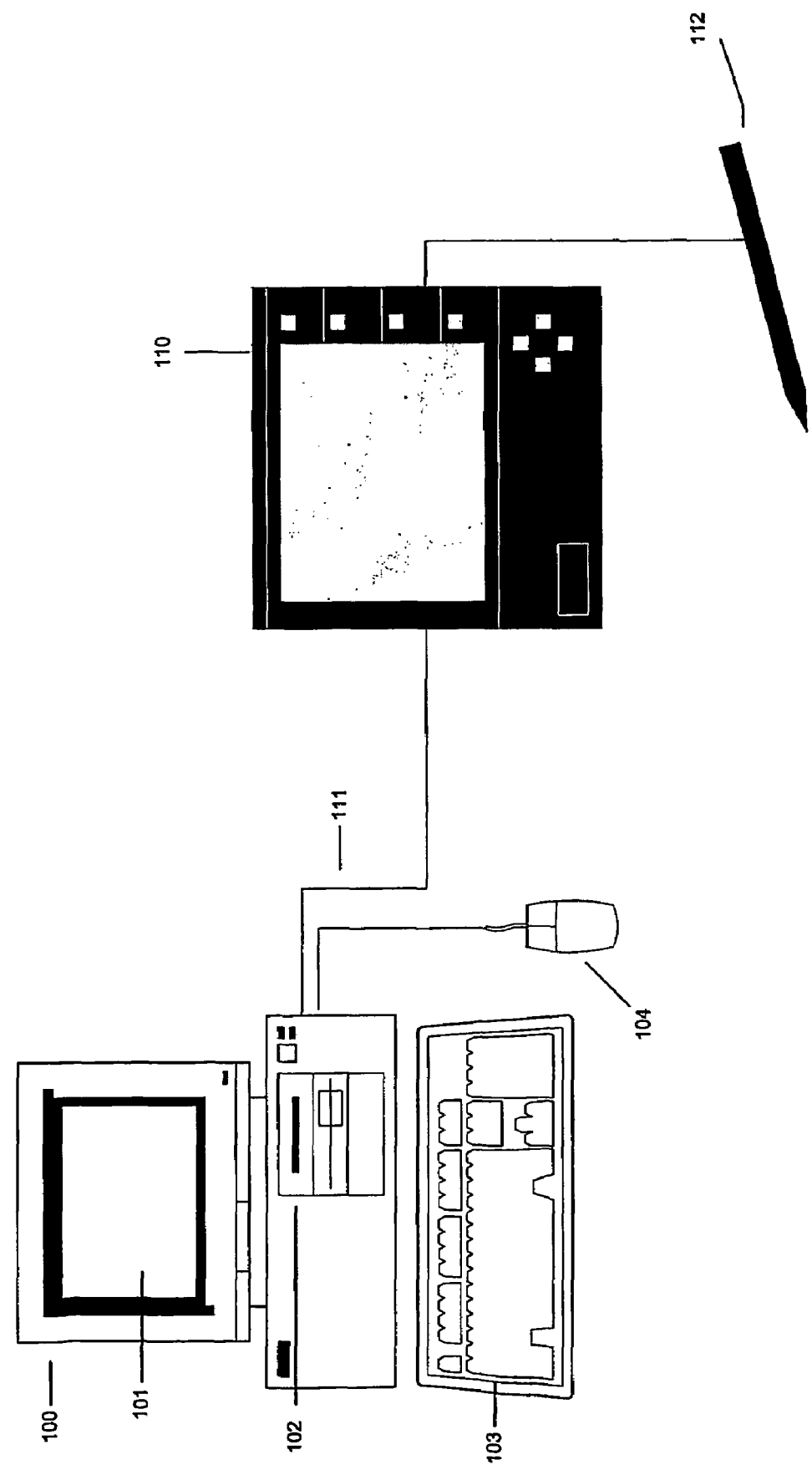
FIG. 1 depicts a typical hardware configuration of an imaging system.

FIG. 1 depicts a typical hardware configuration in accordance with the present invention. Computer system 100 includes monitor 101, CD-ROM 102 containing a library of gold standard images, keyboard 103 and mouse 104. Alternatively, the library of images can be downloaded to computer system 100 over the World Wide Web, and stored on the computer system's hard drive. The imaging part of the system includes box 110 connected to probe 112 and connected to computer system 100 via cable 111. Box 111 could be, for example, an ultrasound generator for creating sonograms. Alternatively, box 111 could be replaced by a plug-in card that attaches directly to the motherboard of computer 100., The system of the invention is not, however, limited to the imaging device depicted.

In a preferred embodiment, the system of the present invention is a software system that is part of the software that controls the imaging equipment, and is installable on computer system 100. Alternatively, the software system of the invention can be a stand-alone system installed from a CD-ROM or downloaded from the web.

The system of the present invention can build a customized mini-library from the library of gold standard images by selecting those gold standard images for the particular models of imaging devices and probes in use. These gold standard images are then available for side by side comparison with images obtained by the user. Thus, with the system and probe in use, a user can see exactly what he or she should target as the gold standard and the system of the invention provides the user with all of the help needed to achieve that standard. Instead of having a medical device that only generates images, the device now shows what is the highest achievable standard and how the user can achieve that standard.

Figure 2:
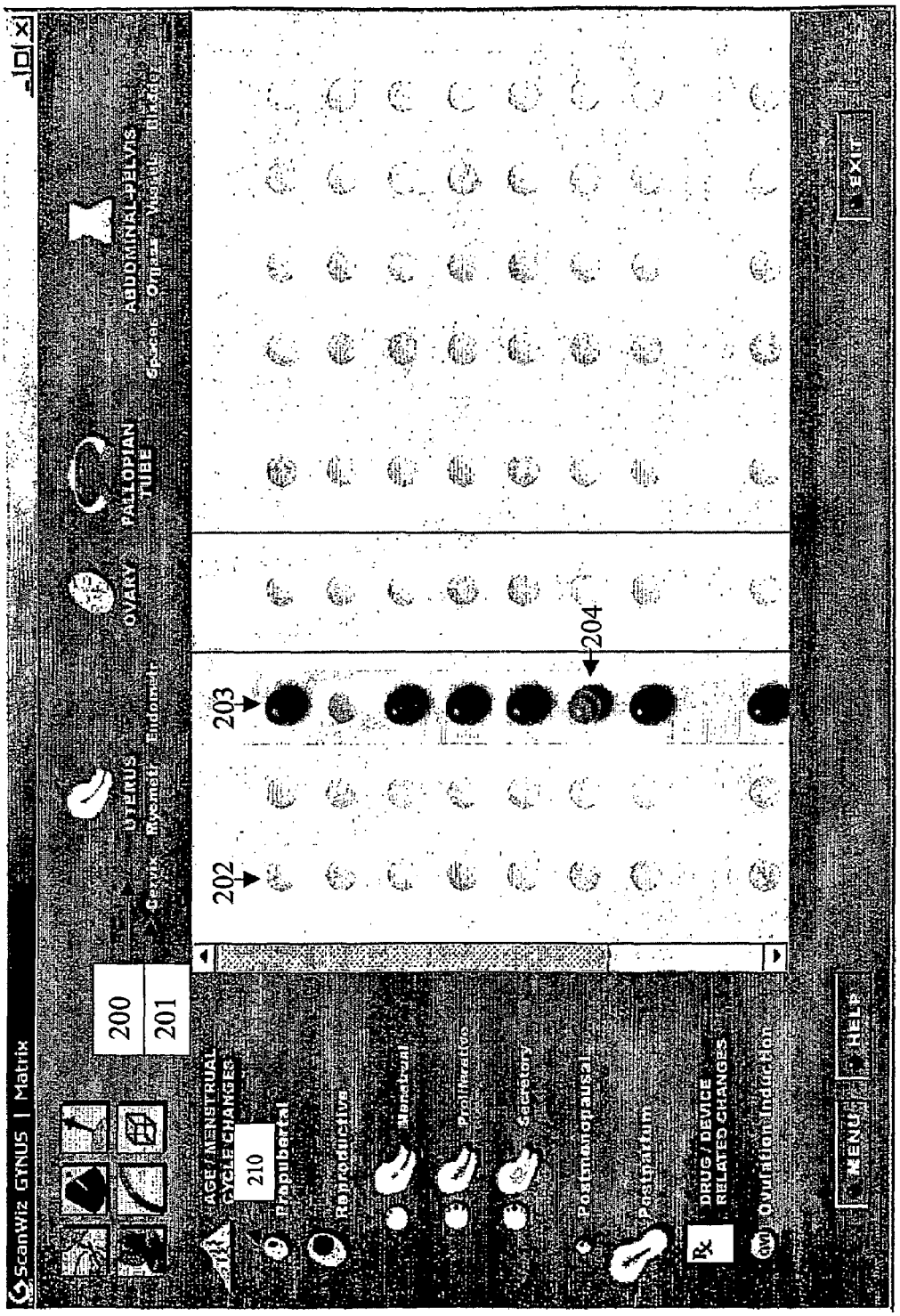
FIG. 2 depicts a typical access matrix for selecting an organ and condition.

FIG. 2 depicts an exemplary screen that is displayed when a user is using the system of the invention to obtain a sonogram of the uterus. A horizontal list 200 of reproductive organs is displayed, in which "Uterus" is highlighted, and underneath a horizontal list 201 of organ sub-parts is displayed, of which "Endometrium" is highlighted. In addition, a vertical list 210 of physiological conditions, of which "Postmenopausal" is highlighted. The screen displays a matrix of balls corresponding to possible selections 202. The column 203 corresponding to "Endometrium" is highlighted, of which the ball 204 corresponding to "Postmenopausal/Endometrium" is selected. The system will thus display the sonogram obtained by the user with the gold standard sonogram of a postmenopausal endometrium obtained from the user's ultrasound generator and probe.

Figure 3:
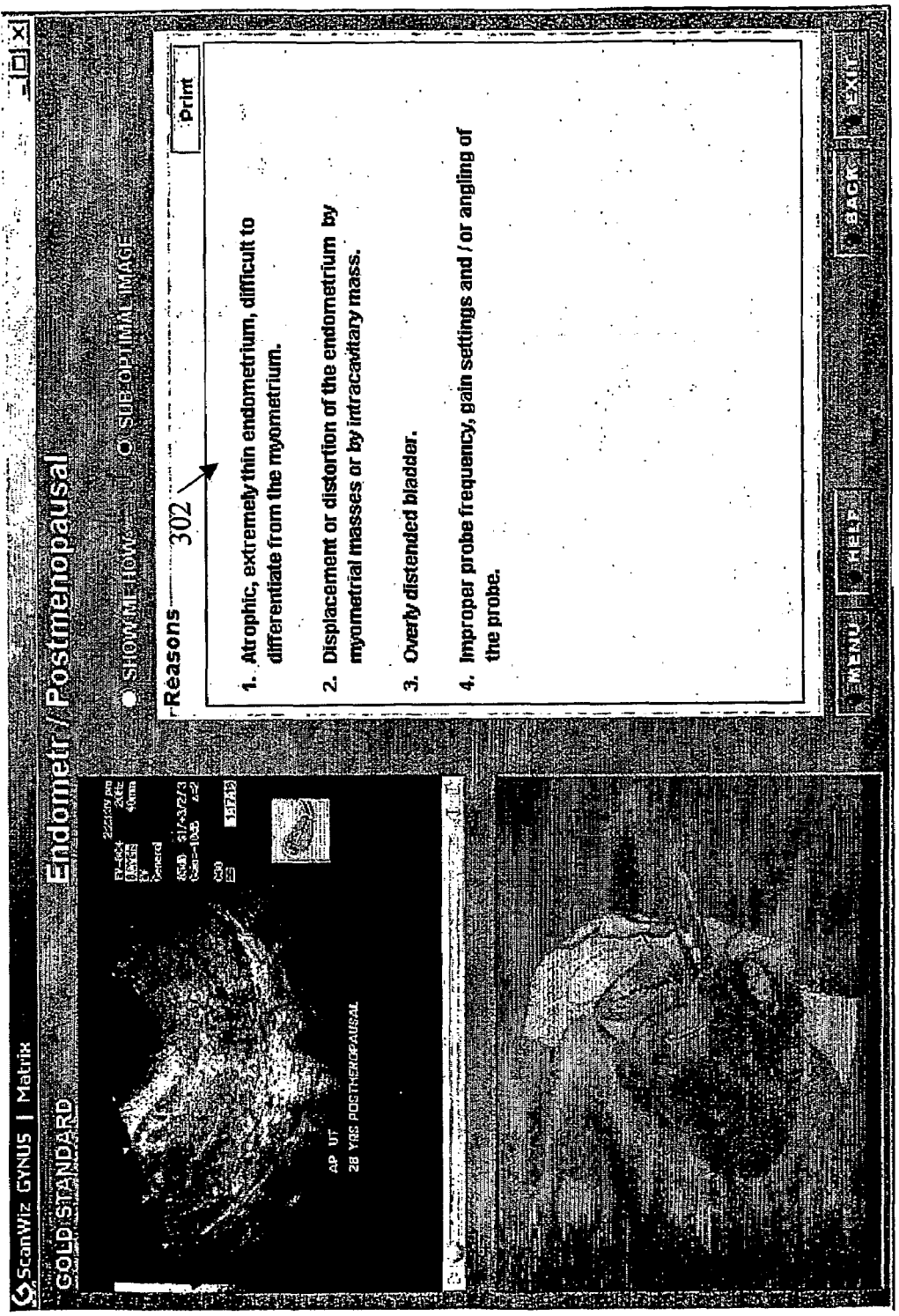
FIG. 3 depicts a gold standard image compared with a user generated image with a list of reasons for a sub-optimal image.
Figure 4:
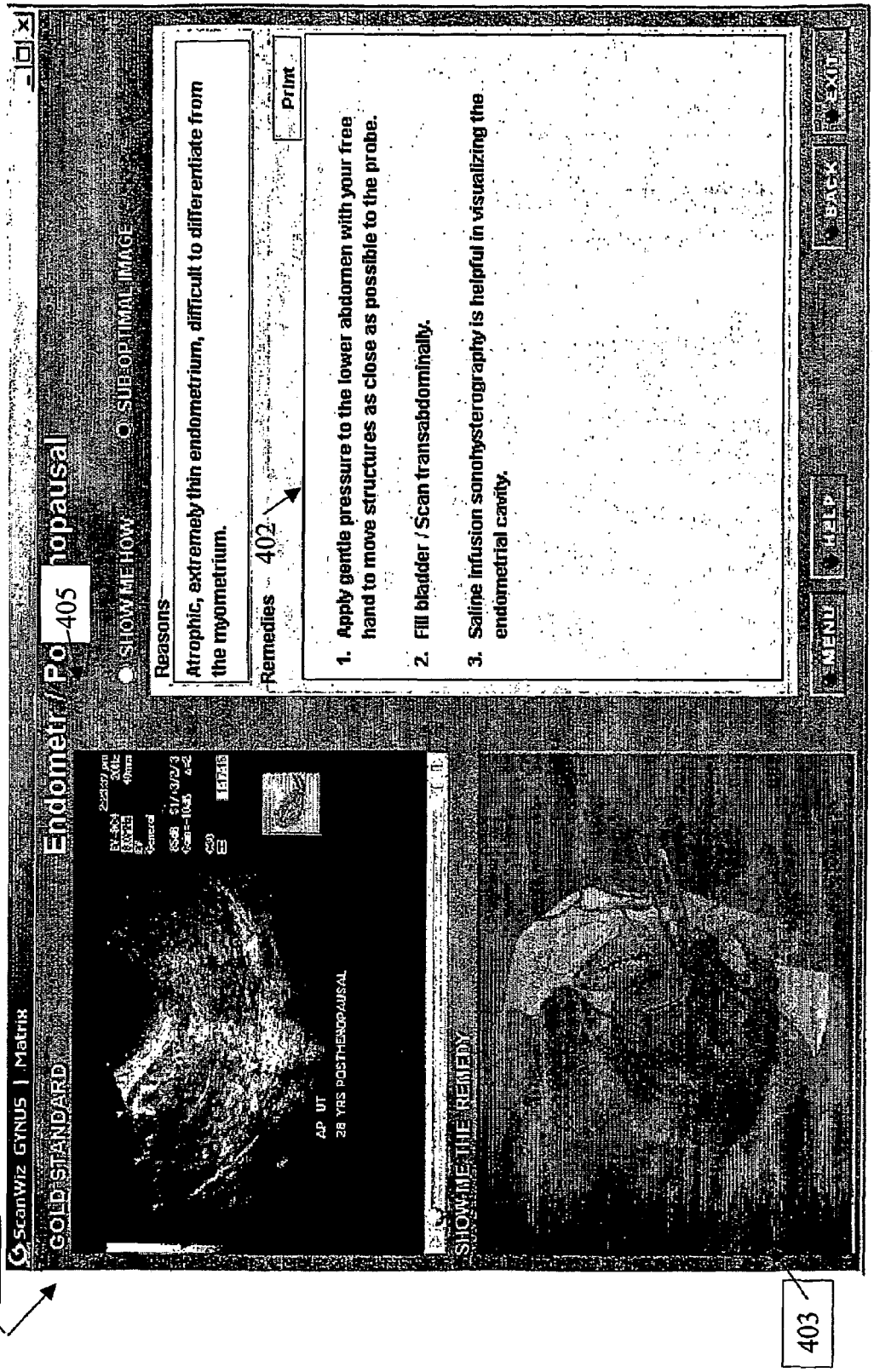
FIG. 4 depicts a list of remedies for upgrading a sub-optimal image.

The invention supports several functions, as illustrated in FIGS. 3-6. For a user not able to achieve an image of gold standard quality, the software can list a series of reasons for situations inferior with respect to the gold standard, as shown in FIG. 3. Examples of these reasons are depicted in the reasons listbox 302 in FIG. 3. Clicking on one of these reasons will present a list of possible problems or reasons for the low quality image, sorted by probability, for the particular organ and/or condition being scanned. By selecting one of the reasons, the system lists possible remedial actions that can be taken to improve the image quality. For example, clicking on the "Atrophic" listing in listbox 302 causes a Remedies listbox 402 to appear as shown in FIG. 4. Listbox 402 displays a list of possible solutions, for example, "Apply gentle pressure . . . ", "Fill bladder . . . ", etc., as shown in the listbox 402. As the user performs the suggested remedy, he or she can continuously monitor the improvement of the generated image 403 in real-time by comparing it with the gold standard image 404. The remedies depicted in listboxes 402 can be associated with hyperlinks to video and audio files that show a user how to perform a suggested maneuver with the equipment in use to solve the problem in real-time.

Figure 5:
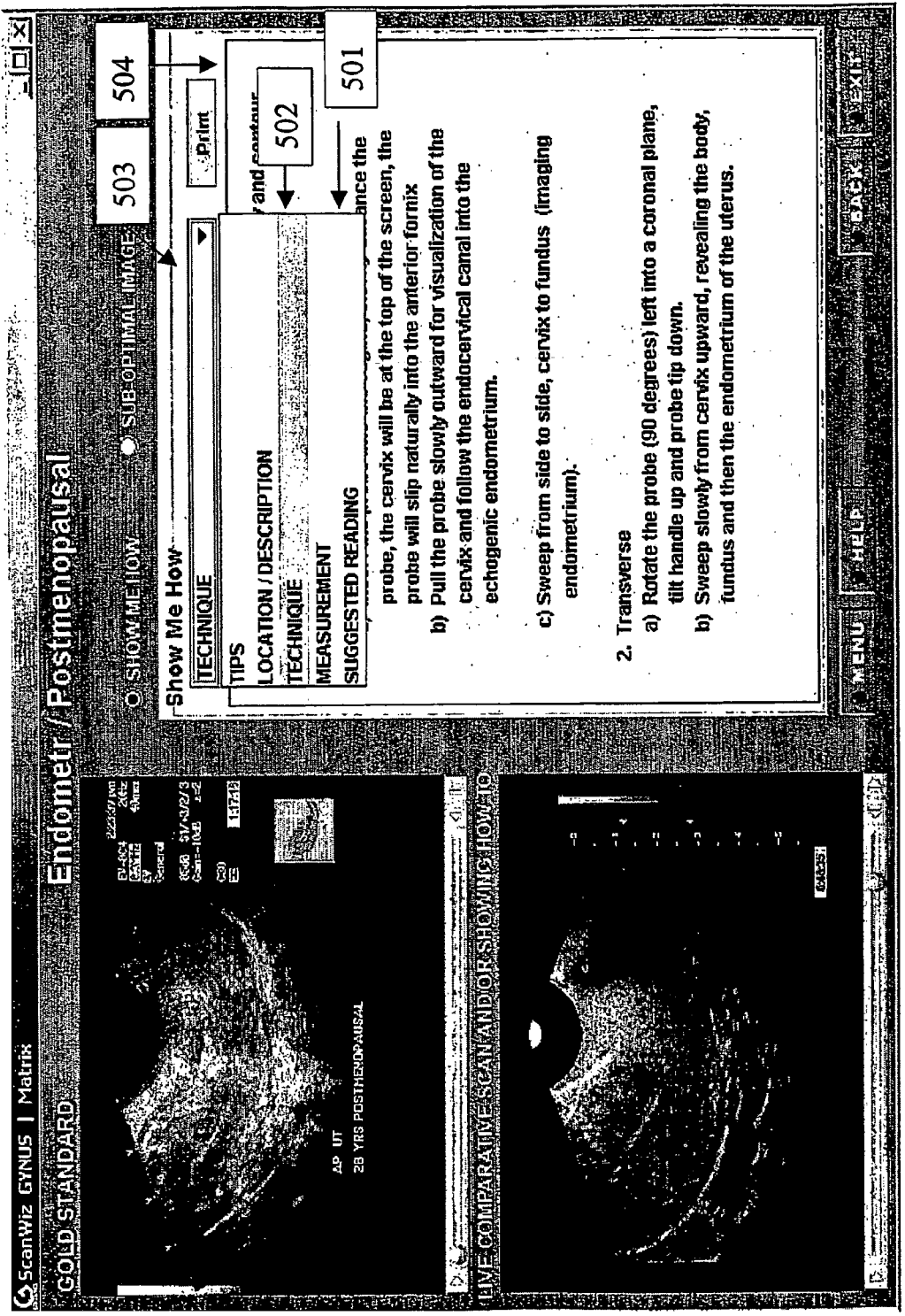
FIG. 5 depicts a list of tips for improving a sub-optimal image.

The invention also includes online help for the user, accessible by clicking on the "Show Me How" button 405 depicted in FIG. 4. FIG. 5 depicts the screen presented to the user after clicking the "Show Me How" button 405. A help menu 501 depicts various help topics, of topic 502, "Technique", is selected and displayed in field 503. Listbox 504 displays descriptions of the proper technique for obtaining a gold standard image.

Figure 6:
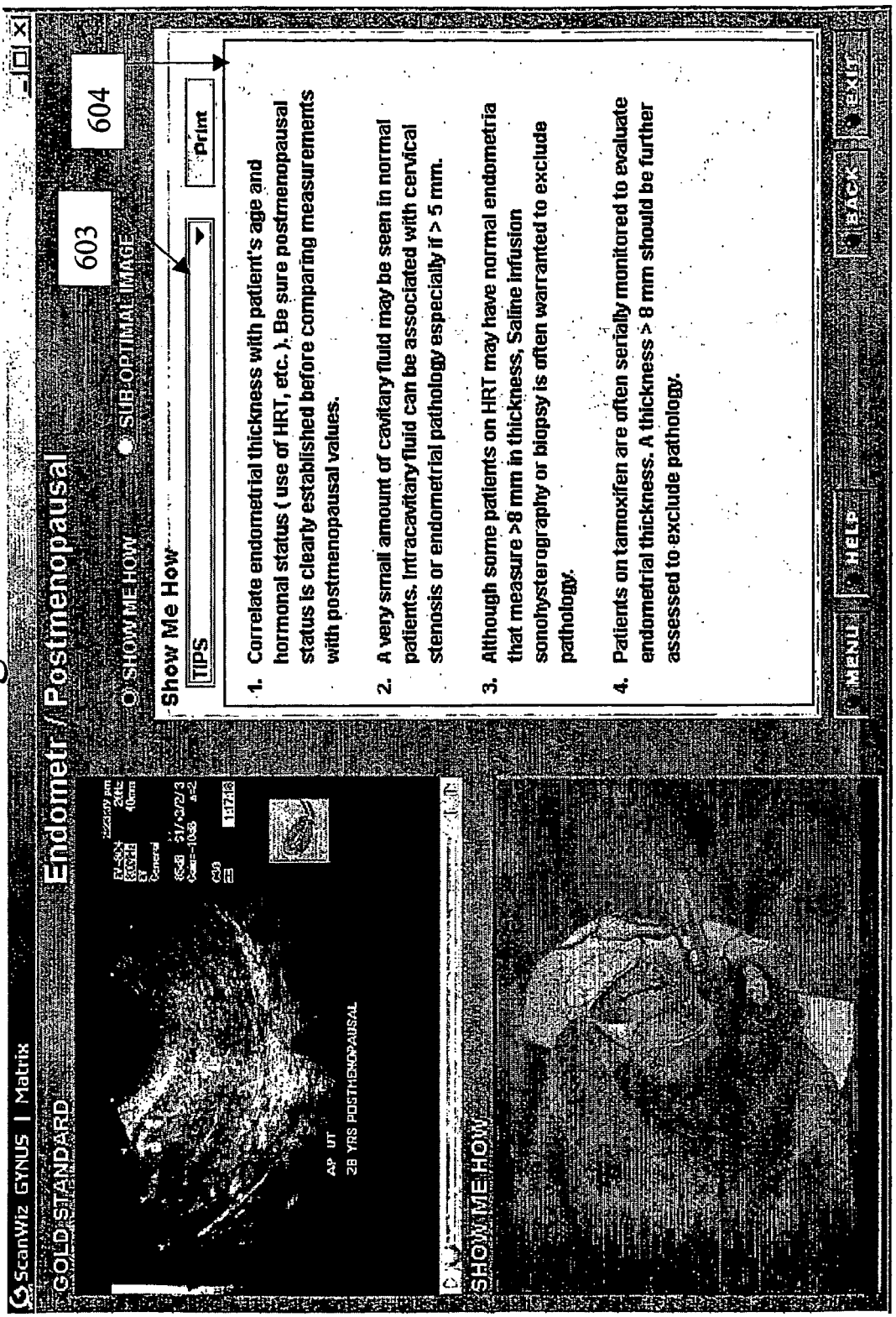
FIG. 6 depicts a list of techniques a user can apply for improving an image.

Alternatively, a user could select the help topic "Tips" in menu 501, which invokes the screen depicted in FIG. 6. The selected help topic, "Tips", is displayed in field 603, while listbox 604 displays a list of various tips for obtaining a gold standard image.

Figure 7:
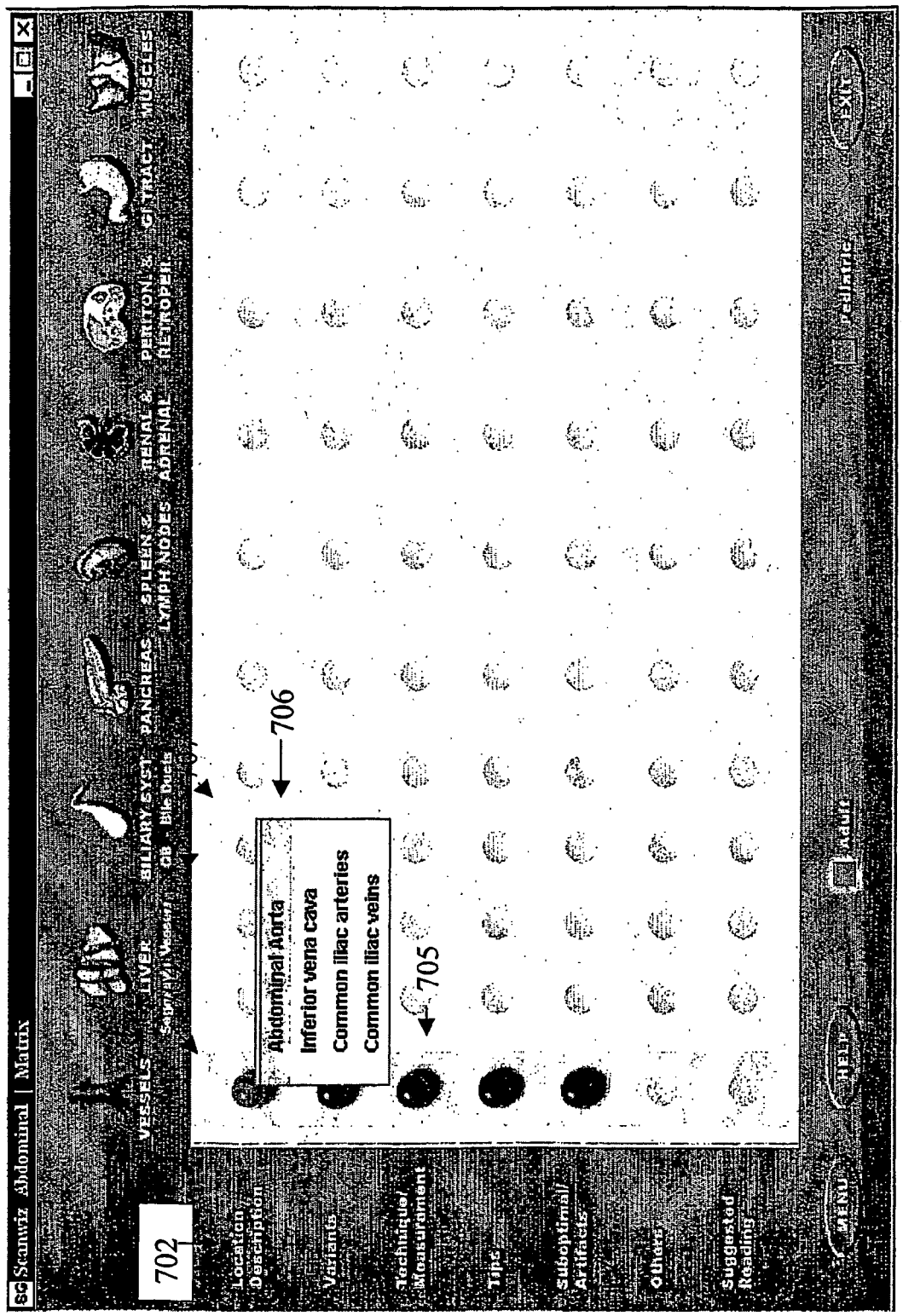
FIG. 7 depicts an alternative access matrix for selecting an organ and condition.
Figure 8:
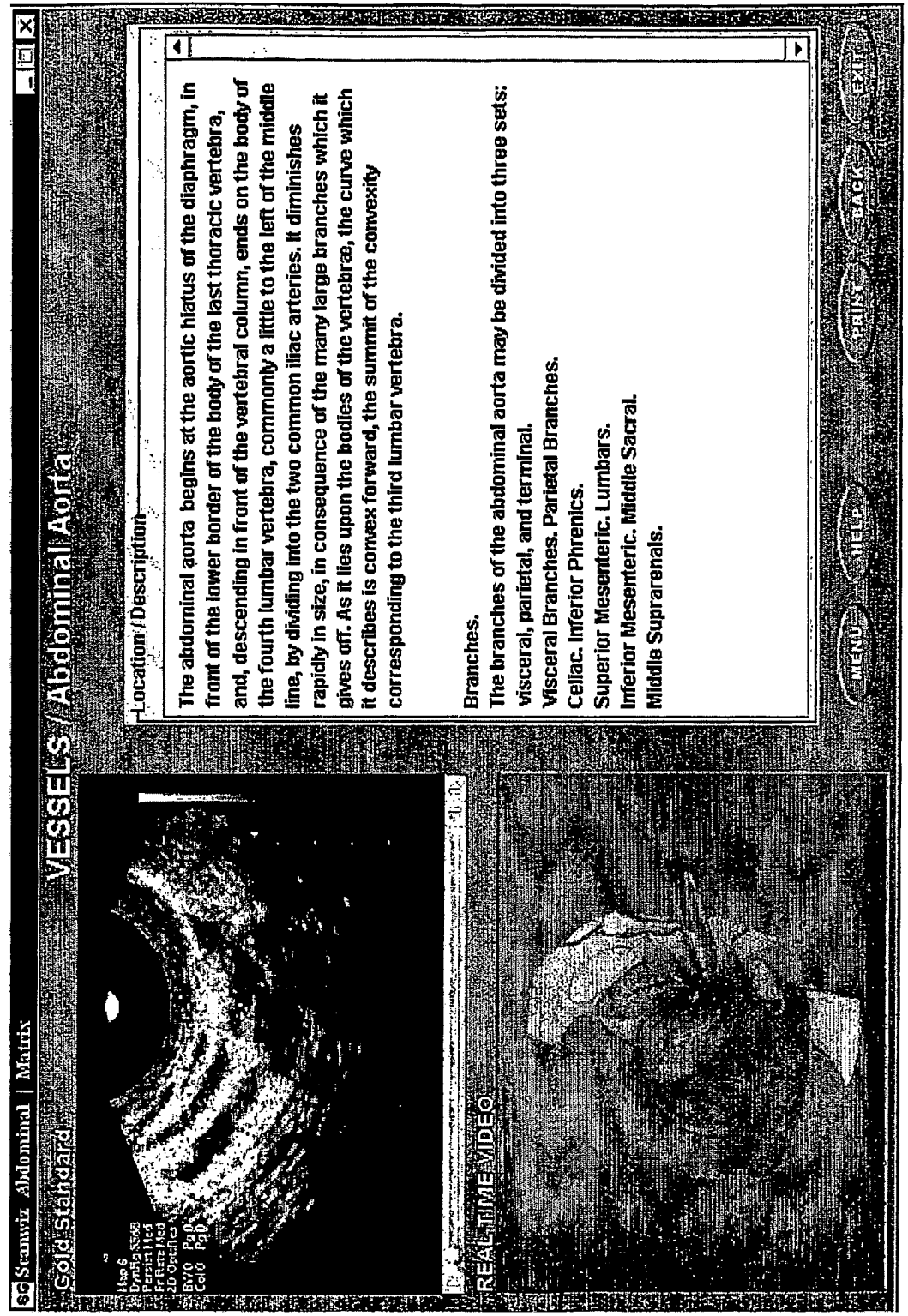
FIG. 8 depicts an real-time video image compared with a gold standard image with a description of the organ being imaged.

FIG. 7 depicts an alternative exemplary screen that is displayed when a user is using the system of the invention to obtain a sonogram of the abdomen. A horizontal list 701 of reproductive organs is displayed, in which "Vessels" is highlighted, along with a vertical list 702 of help topics, of which "Location/Description" is highlighted. The screen displays a matrix of balls corresponding to possible selections 703, of which column 705 corresponding to "Vessels" is highlighted. The ball 704 corresponding to "Location/Description" and "Vessels" is selected. By placing the mouse cursor over the ball 704, a listbox 706 of vessels is displayed, of which selection 707 "Abdominal Aorta" is highlighted. The system will thus display the sonogram obtained by the user with the gold standard sonogram of an abdominal aorta obtained from the user's ultrasound generator and probe, as depicted in FIG. 8. In this example, the system displays a sub-window describing the abdominal aorta and its branches while it is being imaged.

A further feature of the invention is that positioning the mouse cursor over a gold standard image causes text to appear that describes what is depicted in the terminology of the imaging device in use. In the example being described, the image would be described in ultrasound terminology. In addition, graphs or nomograms can also appear.

In a most preferred embodiment, the system of the invention uses pattern recognition technology to freeze a scan when the gold standard is reached. In addition, a user can be informed of the missing items needed to obtain the gold standard in the case of a sub-optimal image. The invention can become a virtual application specialist of the manufacturer of the imaging device, assisting the user to achieve gold standard images in the absence of a technical instructor.

Although the invention has been described in an ultrasound embodiment, the invention is applicable to any imaging device. For example, a camera can be installed in a satellite to look for patterns relating to the use of land for certain crops, such as coffee or cocoa, as well as illegal crops such as coca or marijuana. In this case, the remote controller of the camera uses a library of gold standard images tailored to the recognition of agricultural patterns. Should the gold standard related to the cultivation of a certain crop not be achieved, the device provides a list of problems, such as "Angle too Wide", "Lack of Resolution", etc., and a list of proposed remedies, such as the satellite trajectory to achieve to best angle of view, or to enhance resolution by combining Doppler and laser technology to perform an infrared scan. It will be apparent to the skilled practitioner that use of the invention with any imaging system where the imaging is performed by a human being is within the scope of the invention. The invention is defined by the accompanying claims.

What is claimed is:

1. A system for improving the quality of medical images comprising:
    means for providing a list of a plurality of sub-optimal image situations for an operator's selection;
    for each sub-optimal image situation, means for providing a list of at least one possible reason for said sub-optimal image situation selected by said operator, wherein the list of at least one possible reason is sorted by the probability the reason being the actual cause of the sub-optimal image; and
    for each reason in the list of at least one possible reason, means for providing a list of at least one remedy for said reason to said operator.

2. The system of claim 1, further comprising means for linking a remedy to an audio or video file that contains an explanation or depiction of how to perform said remedy.

3. The system of claim 1, further comprising means for displaying text containing a gold standard image in response to positioning a mouse cursor on said gold standard image.

4. The system of claim 3, further comprising means for displaying a graph in response to said mouse cursor position.

5. The system of claim 1, further comprising pattern recognition means for stopping a scan when a gold standard image has been achieved.

6. The system of claim 5, further comprising means for informing a user of missing items needed to obtain a gold standard image.

* * * * *